United States Patent [19]

Taylor et al.

[11] Patent Number: 4,889,859

[45] Date of Patent: Dec. 26, 1989

[54] PYRIDO[2,3-D]PYRIMIDINE DERIVATIVES

[75] Inventors: Edward C. Taylor, Princeton, N.J.; Chuan Shih, Indianapolis, Ind.

[73] Assignee: The Trustees of Princeton University, Princeton, N.J.

[21] Appl. No.: 156,908

[22] Filed: Feb. 5, 1988

[51] Int. Cl.[4] .................. A61K 31/505; C07D 471/04
[52] U.S. Cl. ..................................... 514/258; 544/279
[58] Field of Search ......................... 544/279; 514/258

[56]  References Cited

U.S. PATENT DOCUMENTS 4,684,653  8/1987  Taylor et al. ...................... 544/279

OTHER PUBLICATIONS

Merck Index (1983) pp. 599 & 1408.

Primary Examiner—Mukund J. Shah
Assistant Examiner—C. L. Cseh
Attorney, Agent, or Firm—Mathews, Woodbridge, Goebel, Pugh & Collins

[57]  ABSTRACT

Derivatives of N-[2-(5,6,7,8-tetrahydropyrido-[2,3-d]pyrimidin-6-yl)-alkyl]benzoyl-L-glutamic acid are antineoplastic agents. A typical embodiment is N-(2-fluoro-4-[2-(2-amino-4-hydroxy-5,6,7,8-tetrahydropyrido-[2,3-d]pyrimidin-6-yl)ethyl]benzoyl)-L-glutamic acid.

14 Claims, No Drawings

PYRIDO[2,3-D]PYRIMIDINE DERIVATIVES

TECHNICAL FIELD

The invention pertains to derivatives of N-[2-(5,6,7,8-tetrahydropyrido[2,3-d]pyrimidin-6yl)-alkyl]benzoyl-L-glutamic acid, which are antineoplastic agents, and to their preparation and use.

BACKGROUND ART

The folic acid antimetabolites aminopterin and amethopterin (also known as 10-methylaminopterin or methotrexate) are antineoplastic agents. These compounds inhibit enzymatic conversions involving metabolic derivatives of folic acid. Amethopterin, for example, inhibits dihydrofolate reductase, an enzyme necessary for the regeneration of tetrahydrofolate from dihydrofolate which is formed during the conversion of 2-deoxy-uridylate to thymidylate by the enzyme thymidylate synthetase.

Other derivatives of folic acid and aminopterin have been synthesized and tested as anti-metabolites. Among these are various "deaza" compounds in which a methylene or methylidene group occupies a position in the molecule normally occupied by an imino or nitrilo group, respectively. These derivatives have varying degrees of antimetabolic activity. 10-Deazaaminopterin is highly active (Sirotak et al., *Cancer Treat. Rep.*, 1978, 62, 1047) whereas 10-deazafolic acid shows no significant activity (Struck et al., *J. Med. Chem.*, 1971, 14, 693). 5-Deazafolic acid is only weakly cytotoxic whereas 5-deazaaminopterin has activity similar to that of amethopterin (Taylor et al., *J. Org. Chem.*, 1983, 48, 4852). 5,6,7,8-Tetrahydro-5-deazaaminopterin also is active (U.S. Pat. No. 4,684,653). 8,10-Dideazafolic acid is only marginally effective as a dihydrofolate reductase inhibitor (De Graw et al., "Chemistry and Biology of Pteridines", Elsevier, 1979, 229) while 5,8,10-trideazafolic acid also shows only marginal activity against mouse L1210 leukemia (Oatis et al., *J. Med. Chem.*, 1977, 20, 1393). 8,10-Dideazaaminopterin is reported to be active (U.S. Pat. No. 4,460,591) and 5,8,10-trideazaaminopterin exhibits activity against mouse L1210 leukemia (Yan et al., *J. Heterocycl. Chem.*, 1979, 16, 541).

DISCLOSURE OF INVENTION

The invention pertains to (i) a tetrahydropyrido[2,3-d]pyrimidine of the formula:

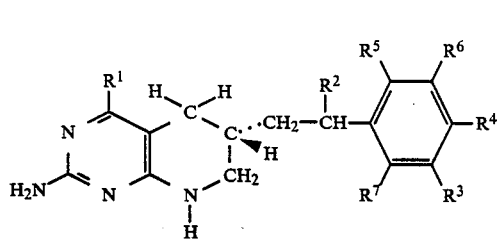

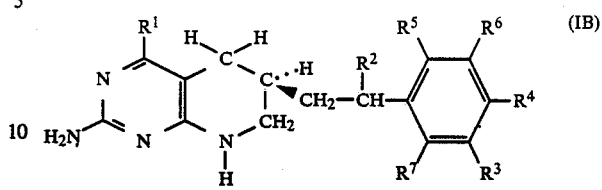

wherein $R^1$ is hydroxy or amino; $R^2$ is hydrogen, methyl, or ethyl; and $R^3$, $R^4$, $R^5$, $R^6$, and $R^7$ are selected such that (a) $R^3$ is

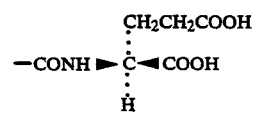

and each of $R^4$, $R^5$, $R^6$, and $R^7$ independently is hydrogen, chloro, or fluoro; or (b) $R^4$ is

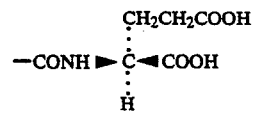

one member of $R^3$, $R^5$, $R^6$, and $R^7$ is chloro or fluoro; and the remaining members of $R^3$, $R^5$, $R^6$, and $R^7$ is hydrogen, chloro, or fluoro;

(ii) the pharmaceutically acceptable alkali metal, alkaline earth, non-toxic metal, ammonium, and substituted ammonium salts thereof; and (iii) diastereoisomeric mixtures of said tetrahydropyrido[2,3-d]pyrimidine or said salts.

The invention also pertains to methods for the preparation of such compounds, to intermediates useful in those preparations, and to methods and compositions for the use of such compounds in combating neoplastic growth.

MODES FOR CARRYING OUT THE INVENTION

The compounds of the invention are derivatives of the pyrido [2,3-d]pyrimidine heterocyclic ring which is numbered as follows:

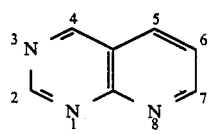

The compounds of Formulas IA and IB exist in tautomeric equilibrium with the corresponding 4-oxo and 4-imino compounds:

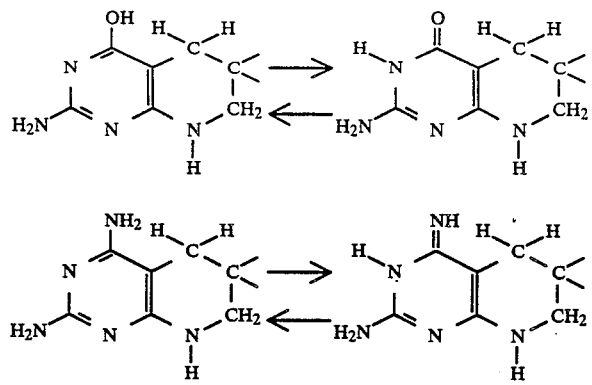

For convenience, the 3,4-dehydro-4-hydroxy and 3,4-dehydro-4-amino forms are depicted, and the corresponding nomenclature is sued, throughout this specification, it being understood that in each case such includes the tautomeric 4(3H)-oxo and imino forms.

The compounds can be prepared by allowing a compound of the formula:

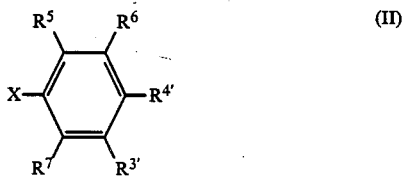

wherein X is bromor or iodo; R³'is

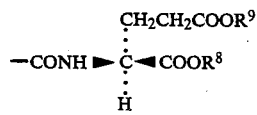

one member of R⁴', R⁵, R⁶, and R⁷ is hydrogen, chloro, or fluoro; or R⁴'is

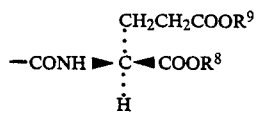

one member of R³', R⁵, and R⁶ is chloro or fluoro;
a second of the remaining members of R³', R⁵, and R⁶ is hydrogen, chloro, or fluoro; and
the remaining member of R³', R⁵, and R⁶ is hydrogen; and
each of R⁸ and R⁹ is a carboxylic acid protecting group, with a compound of the formula:

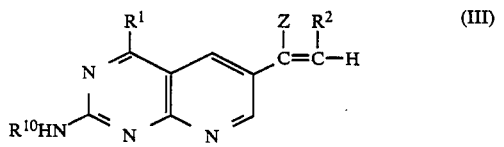

wherein R¹⁰ is hydrogen or an amino protecting group;
Z when taken independently of R² is hydrogen; and
R² when taken independently of Z is hydrogen, methyl or ethyl; or Z and R² when taken together are a carbon-carbon bond;
in the presence of a palladium complex, to yield a compound of the formula:

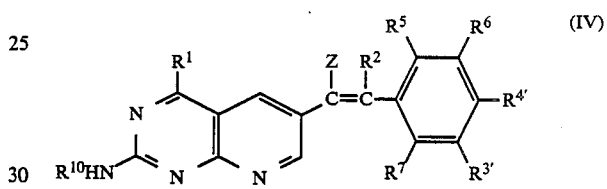

in which R¹, R², R³', R⁴', R⁵, R⁶, R⁷, R¹⁰ and Z are as herein defined.

The palladium complexes are those which have been employed previously in the reaction of aryl halides and allylic alcohols, as described for example by Melpoler et al., *J. Org. Chem.*, 41, No. 2, 1976, 265; Chalk et al., *J. Org. Chem.*, 41, No. 7, 1976, 1206; Arai et al., *J. Heterocyclic Chem.*, 15, 351 (1978); Tamuru et al., *Tetrahedron Papers*, 10, 919 (1978) 919; *Tetrahedron*, 35, 329 (1979). Particularly useful are the palladium/trisubstituted-phosphine complexes of Sakamoto, *Synthesis*, 1983, 312; e.g., a trisubstituted-phosphine such as a triarylphosphine, as for example triphenylphosphine, or a trialkylphosphine; a palladium salt such as palladium acetate or a palladium halide such as palladium chloride; and a cuprous halide, such as cuprous iodide.

The reaction preferably is conducted in the presence of at least one molar equivalent of a secondary or tertiary amine which acts as an acid acceptor, as for example triethylamine, or diethylamine, and under and inert atmosphere, optionally in the presence of an inert polar solvent such as acetonitrile, dimethylformamide, N-methylpyrrolidone and the like. Particularly preferred is the use of acetonitrile which serves as a solvent not only for the reactants but also for the salt formed from the acid acceptor and acid generated. Moderately elevated temperatures, as for example from about 75° to 125° C., preferable at or below 100° C., generally are advantageous.

The amino and carboxylic acid protecting groups discussed herein are those conventionally employed, as described for example by Greene in "Protective Groups in Organic Synthesis", John Wiley & Sons, Inc., 1981, and McOmie in "Protective Groups in organic Chemistry", Plenum Press, 1983. Particularly preferred R¹⁰ protecting groups are alkanoyl groups such as acetyl, propionyl, pivaloyl, and the like.

Catalytic hydrogenation of a compound of Formula IV yields the corresponding 2-amino (or 2-protected amino)-6-substituted-5,6,7,8-tetrahydropyrido[2,3-d]-pyrimidine of the formula:

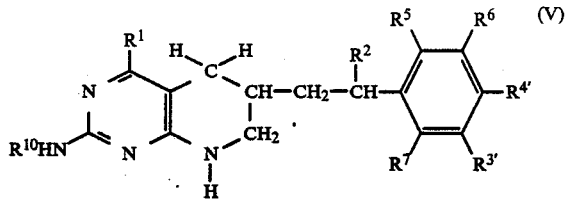

The compounds of Formula V are then subjected to hydrolysis to remove the protecting groups $R^8$, $R^9$ and $R^{10}$. This is conducted at normal temperatures utilizing aqueous acid or base, such as for example, an aqueous alkali metal hydroxide, optionally in the presence of a water miscible organic solvent such as methanol, ethanol, tetrahydrofuran, dimethylformamide, and the like, or an acid, as for example trifluoroacetic acid. When base is used, the cationic moiety of the salt is liberated and the product is formed as the dicationic glutamate salt which can be readily precipitated by adjustment of pH, as through acidification with, for example, acetic acid. The resulting products generally are high melting crystalline or microcrystalline solids.

The absolute configuration about the chiral carbon in the glutamic acid chain in $R^3$ or $R^4$ in Formulas IA and IB is (S) or L, being the same absolute configuration as that about the corresponding alpha carbon atom in L-alanine. In addition, the carbon atom in the 6-position of the 5,6,7,8-tetrahydropyrido-[2,3-d]pyrimidine ring is a chiral center, leading to the two (R,S) and (S,S) diastereomers shown in Formulas IA and IB. The mixture of diastereomers can be utilized therapeutically, both serving as substrates for relevant folate enzymes. The diastereomers can also be separated so as to be in a form substantially free of the other; i.e., in a form having an optical purity of >95%.

The diastereomers can be separated mechanically, as by chromatography or a mixture of diastereomers can be treated with a chiral acid operable form a salt therewith. The resultant diastereoisomeric salts are then separated through one or more fractional crystallizations and thereafter the free base of the cationic moiety of at least one of the separated salts is liberated through treatment with a base and removal of the protecting groups. The liberation of the cation of the salt can be performed as a discrete step before or after the removal of the protecting groups, $R^8$, $R^9$, and $R^{10}$ or concomitantly with the removal of such groups under basic hydrolysis.

Suitable chiral acids include the individual enantiomers of 10-camphorsulfonic acid, camphoric acid, alpha bromocamphoric acid, menthoxyacetic acid, tartaric acid, diacetyltartaric acid, malic acid, pyrrolidine-5-carboxylic acid, and the like.

The starting materials of Formula III can be prepared from the corresponding 6-halopyrido[2,3-d]-pyrimidine in the manner set forth in copending U.S. application Ser. No. 922,511. The hydrogenated starting materials of Formula II can be prepared by coupling the appropriate halobenzoic acid and a protected derivative of L-glutamic acid in the manner described in PCT application WO 86/05181. The coupling reaction utilizes conventional condensation techniques for forming peptide bonds, such as activation of the carboxylic acid through formation of the mixed anhydride, treatment with DCC, or use of diphenylchlorophosphonate.

Representative compounds of the present invention include:

A. N-(3-[2-(2amino-4-hydroxy-5,6,7,8-tetrahydropyrido[2,3-d]pyrimidin-6-yl)ethyl]benzoyl)-L-glutamic acid.

B. N-(3-fluoro-5-[2-(2-amino4-hydroxy-5,6,7,8-tetrahydropyrido[2,3-d]pyrimidin-6-yl)ethyl]benzoyl)-L-glutamic acid.

C. N-(2-fluoro-3-[2-(2-amino-4-hydroxy-5,6,7,8-tetrahydropyrido[2,3-d]pyrimidin-6-yl)ethyl]benzoyl)-L-glutamic acid.

D. N-(2-fluoro-5-[2-(2-amino-4-hydroxy-5,6,7,8-tetrahydropyrido[2,3-d]pyrimidin-6-yl)ethyl]benzoyl)-L-glutamic acid.

E. N-(4-fluoro-5-[2-(2-amino-4-hydroxy-5,6,7,8-tetrahydropyrido[2,3-d]pyrimidin-6-yl)ethyl]benzoyl)-L-glutamic acid F. N-(2-chloro-4-[2-(2-amino-4-hydroxy-5,6,7,8-tetrahydropyrido[2,3-d]pyrimidin-6-yl)ethyl]benzoyl)-L-glutamic acid.

G. N-(3-chloro-4-[2-(2-amino-4-hydroxy-5,6,7,8-tetrahydropyrido[2,3-d]pyrimidin-6-yl)ethyl]benzoyl)-L-glutamic acid.

H. N-(2-fluoro-4-[2-(2-amino-4-hydroxy-5,6,7,8-tetrahydropyrido[2,3-d]pyrimidin-6-yl)ethyl]benzoyl)-L-glutamic acid.

I. N-(3-fluoro-4-[2-(2-amino-4-hydroxy-5,6,7,8-tetrahydropyrido[2,3-d]pyrimidin-6-yl)ethyl]benzoyl)-L-glutamic acid.

J. N-(2,6-difluoro-4-[2(2-amino-4-hydroxy-5,6,7,8-tetrahydropyrido[2,3-d]pyrimidin-6-yl)ethyl]benzoyl)-L-glutamic acid.

K. N-(3,5-difluoro-4-[2-(2-amino-4-hydroxy-5,6,7,8-tetrahydropyrido[2,3-d]pyrimidin-6-yl)ethyl]benzoyl)-L-glutamic acid.

L. N-(2,3-difluoro-4-[2-(2-amino-4hyddroxy-5,6,7,8-tetrahydropyrido[2,3-d]pyrimidin-6-yl)ethyl]-benzoyl)-L-glutamic acid.

M. N-(2,3,5,6-tetrafluoro-4-[2-(2-amino-4-hydroxy-5,6,7,8-tetrahydropyrido[2,3-d]pyrimidin-6-yl)ethyl]-benzoyl)-L-glutamic acid.

The resultant compounds of Formulas IA and IB, including mixtures thereof and their pharmaceutically acceptable alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like, have an effect on one or more enzymes which utilize folic acid, and in particular metabolic derivatives of folic acid, as a substrate. The compounds can be used, alone or in combination, to treat neoplasms including choriocarcinoma, leukemia, adenocarcinoma of the female breast, epidermid cancers of the head and neck, squamous or small-cell lung cancer, and various lymhosarcomas. The compounds can also be used to treat fungoides, psoriasis and other autoimmune conditions such as rheumatoid arthritis which are responsive to methotrexate.

The compounds may be administered either orally or preferably parenterally, alone or in combination with other anti-neoplastic agents, steroids, etc., to a mammal suffering from neoplasm and in need of treatment. Parenteral routes of administration include intramuscular, intrathecal, intravenous or intraarterial. Dosage regimens must be titrated to the particular neoplasm, the condition of the patient, and the response but generally doses will be from about 10 to about 100 mg/day for 5-10 days or single daily administration of 250-500 mg, repeated periodically; e.g. every 14 days. Oral dosage forms include tablets and capsules containing from 1-10 mg of drug per unit dosage. Isotonic saline solutions containing 20-100 mg/ml can be used for parenteral administration.

Representative $IC_{50}$ values determined in whole cell human leukemia cell line (CCRF-CEM) are as follows:

| Compound | $IC_{50}$ (mcg/mL) |
| --- | --- |
| A | 0.015 |
| D | 0.100 |
| F | 0.027 |
| H | 0.004 |

Mice implanted with C3H mammary adenocarcinoma were treated intraperitoneally for five days with compound H. At a dosage of 30 mg/kg, 72% inhibition was observed. At a dosage of 100 mg/kg, 80% inhibition was observed. No toxicity was observed at these dosages.

The following inhibitory data were observed with Compound H in 6C3HED lymphosarcoma in mice:

| 6C3HED LYMPHOSARCOMA | | |
| --- | --- | --- |
| DOSE (MK/KG) | % INHIBITION | TOXIC/TOTAL |
| 200 | 100 | 0/10 |
| 100 | 100 | 0/10 |
| 50 | 95 | 0/10 |
| 25 | 94 | 0/9 |

The following examples will serve to further illustrate the invention. In the NMR data, "s" denotes singlet, "d" denotes doublet, "t" denotes triplet, "q" denotes quartet, and "m" denotes multiplet.

EXAMPLE 1

A mixture of 0.016 g (0.093 mmol) of palladium chloride and 0.0486 g (0.185 mmol) of triphenylphosphine in 5 mL of acetonitrile is stirred under nitrogen at room temperature for 30 minutes. To this mixture is added an additional 10 mL of acetonitrile and 0.80 g (1.89 mmol) of dimethyl N-(2-fluoro-5-iodobenzoyl)L-glutamate, 0.50 g (1.85 mmol) of 2-pivaloylamino-4-hydroxy-6-ethynylpyrido[2,3-d]pyrimidine, 0.0088 g (0.046 mmol) of copper iodide, and 0.54 mL (3.89 mmol) of triethylamine. The mixture is then heated to reflux for 3 hours. After cooled to room temperature, the solvent is removed in vacuo and the residue is flash chromatographed on silica gel using 1:19 methanol:chloroform as the eluent to yield 0.92 g (88%) of dimethyl N-(2-fluoro-5-[2-(2-pivaloylamino-4-hydroxypyrido[2,3-d]pyrimidin-6-yl)-ethynyl]-benzoyl)-L-glutamate as a dark yellow solid m.p. 189°-191° C. (dec); $R_f$=0.48 (1:19 methanol:chloroform), Mass (FD)=565; IR (KBr, cm$^{-1}$)=1146, 1228, 1263, 1440, 1488, 1549, 1596, 1607, 1622, 1673, 1742; UV (EtOH) $\lambda_{max}$=319 (epsilon=30600), 259 (epsilon=11200), 212 (epsilon=42100); $^1$NMR (300 MHz, CDCl$_3$) delta 1.38 (s, 9H), 2.19 (m, 1H), 2.3-2.6 (m, 3H), 3.72 (s, 3H), 3.85 (s, 3H), 4.95 (m, 1H), 7.21 (dd, 1H, J=8.5, 11.2 Hz), 7.45 (m, 1H), 7.68 (m, 1H), 8.26 (dd, 1H, J=2.0, 7.2 Hz), 8.37 (s, 1H), 8.63 (d, 1H, J=2.2 Hz), 9.0 (d, 1H, J=2.0 Hz).

EXAMPLE 2

A sample of 0.115 g (0.202 mmol) of dimethyl N-(2-fluoro-5-[2-(2-pivaloylamino-4-hydroxypyrido-[2,3-d]pyrimidin-6-yl)ethynyl]-benzoyl)-L-glutamate and 0.045 g of platinum oxide is dissolved in 5 mL of glacial acetic acid. This mixture then is hydrogenated under atmospheric hydrogen at room temperature for 5 hours. The catalyst is removed by filtration, and the filtrate concentrated in vacuo, and the crude solid flash chromatographed on silica gel using 1:19 methanol: chloroform as the eluent to yield 0.76 g (66%) of dimethyl N-(2-fluoro-5-[2-2-pivaloylamino-4-hydroxy-5,6,7,8-tetrahydropyrido[2,3-d]pyrimidin-6-yl)ethyl]benzoyl)-L-glutamate as a gray-white solid. m.p. 165-170° C. (dec); $R_f$=0.33 (1:19 methanol:chloroform), Mass (FD)=573; IR (KBr, cm$^{-1}$)=1161, 1205, 1223, 1232, 1439, 1460, 1478, 1492, 1527, 1536, 1556, 1573, 1619, 1645, 1743, 3392, 3395; UV (EtOH) $\lambda_{max}$=271 (epsilon=10200), 234 (epsilon=42900).

Anal. Calcd. for $C_{28}H_{36}N_5O_7F$: C, 58.63; H, 6.33; N, 12.21. Found: C, 58.59; H, 6.38; N, 12.14.

$^1$NMR (300 MHz, CDCl$_3$) delta 1.32 (s, 9H), 1.73 (m, 2H), 1.89 (m, 1H), 2.20 (m, 2H), 2.30-2.60 (m, 3H), 2.65-2.90 (m, 3H), 3.03 (m, 1H), 3.39 (m, 1H), 3.70 (s, 3H), 3.83 (s, 3H), 4.66 (s, 1H), 4.91 (m, 1H), 7.09 (dd, 1H, J=8.4, 11.7 Hz), 7.36 (m, 2H), 7.75 (s, 1H), 7.91 (dd, 1H, J=2.2, 7.4 Hz).

EXAMPLE 3

A sample of 0.024 g (0.042 mmol) of dimethyl N-(2-fluoro-5-[2-2-pivaloylamino-4-hydroxy-5,6,7,8-tetrahydropyrido[2,3-d]pyrimidin-6-yl)ethyl]benzoyl)-L-glutamate is dissolved in 0.5 mL of 1N sodium hydroxide and stirred at room temperature for 5 days. The pale yellow solution then is acidified with glacial acetic acid and the solvent removed in vacuo. The residue is triturated with water and the solid collected by suction filtration, washed with a small amount of water, and dried in vacuo at 100° C. to give 0.4 g (73%) of N-(2-fluoro-5-[2-(2-amino-4-hydroxy-5,6,7,8-tetrahydropyrido[2,3-d]-pyrimidin-6-yl)ethyl]benzoyl)-L-glutamic acid as a white solid. m.p. 252°-262° C. (dec); $R_4$=0.04 (1:19 methanol: chloroform), Mass (FAB)=462; IR (KBr, cm-hu −1)=1230, 1248, 1263, 1307, 1349, 1379, 1398, 1462, 1442, 1544, 1616, 1650, 1705, 2928; UV (EtOH) $\lambda_{max}$=278 (epsilon=13300), 221 (epsilon=29800); $^1$NMR (300 MHz, Me$_2$SO-d6) delta 1.57 (brs, 3H), 1.70-2.10 (m, 4H), 2.34 (t, 2H J=5.0 Hz), 2.60-2.85 (m, 3H), 3.20 (m, 1H), 4.37 (m, 1H), 5.92 (s, 1H), 6.26 (s, 1H), 7.19 (t, 1H, J=9.2 Hz), (brs 1H), 7.45 (d, 1H, J=6.0 Hz), 8.43 (d, 1H, J=6.3 Hz), 9.70 (brs, 1H).

EXAMPLE 4

By substituting a substantially molar equivalent amount of dimethyl N-(3-iodobenzoyl)-L-glutamate for dimethyl N-(2-fluoro-5-iodobenzoyl)-L-glutamate in the procedure of Example 1 there is obtained dimethyl N-(3-[2-(2-pivaloylamino-4-hydroxypyrido[2,3-d]-pyrimidin-6-yl)ethynyl]benzoyl)-L-glumate, m.p. 161°-166° C.

Anal. Calcd. for $C_{28}H_{29}N_5O_7$: C, 61.42; H, 5.38; N, 12.77. Found: C, 61.34; H, 5.23; N, 12.67.

Upon hydrogenation of this material substantially in the manner described in Example 2 there then is obtained dimethyl N-(3-[2-(2-pivaloylamino-4-hydroxy-5,6,7,8-tetrahydropyrido[2,3-d]pyrimidin-6-yl)ethyl]-benzoyl)-L-glutamate, m.p. 141°–148° C.

Anal. Calcd. for $C_{28}H_{37}N_5O_7$: C, 60.53; H, 6.71; N, 12.60. Found: C, 60.26; H, 6.74; N, 12.37.

Hydrolysis as described in Example 3 then yields N-(3-[2-(2-amino-4-hydroxy-5,6,7,8-tetrahydropyrido[2,3-d]pyrimidin-6-yl)ethyl]benzoyl)-L-glutamic acid, m.p. 258°–266° C.; $[\alpha]_{25}{}^D = +11.823$.

EXAMPLE 5

A mixture of 0.44 g (2.56 mmol) of palladium chloride and 1.34 g (5.12 mmol) of triphenylphosphine in 200 mL of acetonitrile is stirred under nitrogen at room temperature for 30 minutes. To this mixture is added an additional 150 mL of acetonitrile, 22.09 g (52.2 mmol) of dimethyl N-(2-fluoro-4-iodobenzoyl)-L-glutamate, 13.830 g (51.2 mmol) of 2-pivaloylamino-4-hydroxy-6-ethynylpyrido[2,3-d]pyrimidine, 0.0244 g (1.28 mmol) of copper iodide, and 15 mL (107.5 mmol) of triethylamine. The reaction mixture is then heated at reflux for 3 hours and then cooled to room temperature, the solvent is then removed in vacuo and the crude solid chromatographed on silica gel with 1:19 methanol:methylene chloride to give 18.1 g (62.5%) of dimethyl N-(2-fluoro-4-[2-(2-pivaloylamino-4-hydroxypyrido[2,3-d]-pyrimidin-6-yl)ethynyl]-benzoyl)-L-glutamate as a white solid m.p. 204°–207° C. (dec); $R_f$=0.60 (1:19 methanol: chloroform), Mass (FD)=565; IR (KBr, cm$^{-1}$)=813, 1151, 1201, 1270, 1375, 1444, 1481, 1490, 1527, 1548, 1598, 1623, 1649, 1670, 1741, 1753; UV (EtOH) $\lambda_{max}$=325 (epsilon=41100), 266 (epsilon=14600), 210 (epsilon=35700).

Anal. Calcd. for $C_{28}H_{28}N_5O_7F$: C, 59.46; H, 4.99; N, 12.38. Found: C, 58.72; H, 4.85; N, 12.90.

$^1$HNMR (300 MHz, CDCl$_3$) delta 1.34 (s, 9H), 2.15 (m, 1H), 2.3–2.55 (m, 3H), 3.67 (s, 3H), 3.80 (s, 3H), 4.87 (m, 1H), 7.37 (m, 2H), 8.07 (t, 1H 9.0 Hz), 8.28 (s, 1H), 8.63 (d, 1H, J=2.6 Hz), 8.98 (d, 1H, J=2.2 Hz).

EXAMPLE 6

Six grams (0.0106 mmol) of dimethyl N-(2-fluoro-4-[2-(2-pivaloylamino-4-hydroxypyrido[2,3-d]-pyrimidin-6-yl)ethynyl]-benzoyl)-L-glutamate and 21 g of platinum oxide are dissolved in 480 mL of glacial acetic acid and hydrogenated at 60 psi for 2 hours. This catalyst removed by filtration, the filtrate concentrated in vacuo, and the residue chromatographed on silica gel to give 4.57 g (75%) of dimethyl N-(2-fluoro-4-[2-2-pivaloylamino-4-hydroxy-5,6,7,8-tetrahydropyrido-[2,3-d]pyrimidin-6-yl)ethyl]benzoyl)-L-glutamate as a white solid. m.p. 183°–191° C. (dec); $R_f$=0.21 (1:19 methanol:chloroform), Mass (FD)=573; IR (KBr, cm$^{-1}$)=1460, 1572, 1577, 1624, 1645, 1738; UV (EtOH) $\lambda_{max}$=270 (epsilon=11100), 235 (epsilon=49500).

Anal. Calcd. for $C_{28}H_{36}N_5O_7F$: C, 58.63; H, 6.33; N, 12.21. Found: C, 58.34; H, 6.35; N, 12.04.

$^1$NMR (300 MHz, CDCl$_3$) delta 1.28 (s, 9H), 1.66 (m, 2H), 1.82 (m, 1H), 2.15 (m, 2H), 2.30–2.55 (m, 3H), 2.65–2.90 (m, 3H), 3.0 (m, 1H), 3.35 (m, 1H), 3.65 (s, 3H), 3.78 (s, 3H), 4.63(s, 3H), 4.85 (m, 1H), 6.96 (d, 1H, J=8.0 Hz), 7.77 (s, 1H), 7.96 (t, 1H, J=8.0 Hz).

EXAMPLE 7

A solution of 0.50 g (0.872 mmol) of dimethyl N-(2-fluoro-4-[2-2-pivaloylamino-4-hydroxy-5,6,7,8-tetrahydropyrido[2,3-d]pyrimidin-6-yl)ethyl]benzoyl)-L-glutamate in 7.5 mL of 1N sodium hydroxide is stirred at room temperature for 66 hours. The solution is acidified with glacial acetic acid, the solvent removed in vacuo and the solid triturated in 10 mL of cold water. The solid is collected by filtration, washed with cold water, ether, and 10 mL of methanol to yield 0.376 g (93%) of N-(2-fluoro-4-[2-(2-amino-4-hydroxy-5,6,7,8-tetrahydropyrido[2,3-d]pyrimidin-6-yl)ethyl]benzoyl)-L-glutamic acid as a pale yellow solid, m.p. 199°–209° C., after drying in vacuo at 100° C.; $R_f$=0.04 (1:1 methanol:chloroform), Mass (FAB)=462; IR (KBr, cm$^{-1}$)=1315, 1389, 1401, 1495, 1542, 1545, 1555, 1565, 1584, 1627, 1647, 1718, 1721, 1724, 3290, 3306, 3310; UV (EtOH) $\lambda_{max}$=278 (epsilon=13700), 223 (epsilon=30900); HNMR (300 MHz, Me$_2$SO—d6) delta 1.57 (brs, 3H), 1.75–1.95 (m, 2H), 2.07 (m, 1H), 2.34 (t, 2H J=7.3 Hz), 2.6–2.9 (m, 3H), 3.20 (m, 2H), 4.39 (m, 1H), 5.92 (s, 2H), 6.26 (s, 1H), 7.15 (dd, 2H, J=6.5, 10.1 Hz), 8.40 (d, 1H, J=7.0 Hz), 9.68 (brs, 1H).

EXAMPLE 8

By substituting a substantially molar equivalent amount of dimethyl N-(2-chloro-4-bromobenzoyl)-L-glutamatic acid for dimethyl N-(2-fluoro-4-iodobenzoyl)-L-glutamate in Example 5, there is obtained dimethyl N-(2-chloro-4-[2-(2-pivaloylamino-4-hydroxypyrido[2,3-d]pyrimidin-6yl)ethynyl]benzoyl)-L-glumate, m.p. 150°–156° C. (dec); $R_f$=0.35; Mass (FD)=581; IR (KBr, cm$^{-1}$)=810, 1147, 1210, 1223, 1245, 1375, 1440, 1446, 1491, 1548, 1593, 1624, 1680, 1741; UV (EtOH) $\lambda_{max}$=323 (epsilon=33200), 264 (epsilon=12400); $^1$HNMR (300 MHz, CDCl$_3$) delta 1.39 (s, 9H), 2.33 (m, 1H), 2.39–2.60 (m, 3H), 3.72 (s, 3H), 4.94 (m, 1H), 7.25(d, 1H, J=10 Hz), 7.53 (dd, 1H, J=1.0, 8.0 Hz), 7.63 (s, 1H), 7.72 (d, 1H, J=7.94) 8.45 (s, 1H), 8.64 (d, 1H, J=2.2 Hz), 8.89 (d, 1H, J=2.0 Hz).

Upon hydrogenation of this product as described in Example 6, there is obtained dimethyl N-(2-chloro-4-[2-(2-pivaloylamino-4-hydroxy-5,6,7,8-tetrahydropyrido[2,3-d]pyrimidin-6-yl)ethyl]benzoyl)-L-glutamate, m.p. 165°–170° C. (dec); $R_f$=0.33 (1:19 methanol:chloroform), Mass (FD)=573; IR (KBr, cm$^{-1}$)=1161, 1205, 1223, 1232, 1439, 1460, 1478, 1492, 1527, 1536, 1556, 1573, 1619, 1645, 1743, 3392, 3395; UV (EtOH) $\lambda^{max}$=271 (epsilon=10200), 234 (epsilon=42900).

Anal. Calcd. for $C_{28}H_{36}N_5O_7F$: C, 58.63; H, 6.33; N, 12.21. Found: C, 58.59; H, 6.38; N, 12.14.

$^1$NMR (300 MHz, CDCl$_3$) delta 1.32 (s, 9H), 1.73 (m, 2H), 1.89 (m, 1H), 2.20 (m, 2H), 2.30–2.60 (m, 3H), 2.65–2.90 (m, 3H), 3.03 (m, 1H), 3.39 (m, 1H), 3.70 (s, 3H), 3.83 (s, 3H), 4.66 (s, 1H), 4.91 (m, 1H), 7.09 (dd, 1H, J=8.4, 11.7 Hz), 7.36 (m, 2H), 7.75 (s, 1H), 7.91 (dd, 1H, J=2.2, 7.4 Hz).

Hydrolysis of the last mentioned compound substantially as described in Example 7 then yields N-(2-chloro-4-[2-(2-amino-4-hydroxy-5,6,7,8-tetrahydropyrido[2,3-d]pyrimidin-6-yl)ethyl]benzoyl)-L-glutamic acid, m.p. 204°–211° C. (dec); $R_f$=0.04 (1:19 methanol: chloroform), Mass (FAB)=478; IR (KBr, cm$^{-1}$)=1263, 1311, 1351, 1357, 1396, 1455, 1486, 1555, 1609, 1650, 1723, 2925, 2929; UV (EtOH) $\lambda_{max}$=278 (epsilon=8000), 219 (epsilon=20400); HNMR (300 MHz, Me$_2$SO—d6) delta 1.56 (brs, 3H), 1.85 (m, 2H), 2.05 (m, 1H), 2.36 (t, 2H J=7.2 Hz), 2.66–2.85 (m, 3H), 3.17 (m, 2H), 4.37 (m, 1H), 5.92 (s, 2H), 6.26 (s, 1H), 7.20–7.40 (m, 3H), 8.63 (d, 1H, J=7.8 Hz), 9.70 (brs 1H).

EXAMPLE 9

The glutamate derivatives employed in the foregoing examples can be prepared as follows:

To 20 mL of benzene are added 2.0 g (0.00752 mol) of 2-fluoro-4-iodobenzoic acid, followed by 2.3 mL (320 mmol) of thionyl chloride and several drops of dimethylformamide. The mixture is heated at reflux of 3.5 hours. The solvent is then removed in vacuo and the residue pumped dry. The resulting acid chloride is redissolved in 10 ml of methylene chloride, and added dropwise to cooled mixture of 1.67 g (7.89 mmol) of L-glutamic acid dimethyl ester hydrochloride, 5 mg of 4-dimethylaminopyridine, and 2.2 mL (15.8 mmol) of triethylamine in 30 mL of methylene chloride. After the addition, the reaction stirred at room temperature for 18 hours. The reaction mixture is then diluted with additional methylene chloride, washed with 1N hydrochloric acid, water and 5% sodium bicarbonate and dried over sodium sulfate. The solvent is removed in vacuo to give 2.34 g (74%) of dimethyl N-(2-fluoro-4-iodobenzoyl)-L-glutamate as a white solid m.p. 94°–96° C.; IR (KBr, cm$^{-1}$)=1159, 1177, 1194, 1208, 1229, 1398, 1437, 1477, 1537, 1601, 1642, 1728, 1739, 1756, 3326.

Anal. Calcd. for $C_{14}H_{15}NO_5FI$: C, 39.74; H, 3.57; N, 3.31. Found: C, 39.98; H, 3.61; N, 3.27.

$^1$HNMR (300 MHz, CDCl$_3$) delta 2.15 (m, 1H), 2.33–2.49 (m, 1H), 3.66 (s, 3H), 3.79 (s, 3H), 4.86 (m, 1H), 7.55 (d, 1H, J=11 Hz), 7.63 (d, 1H, J=8.0 Hz), 7.76 (t, 1H, J=8.0 Hz).

Similarly prepared are dimethyl N-(2-fluoro-5-iodobenzoyl)-L-glutamate, m.p. 69°–72° C., and dimethyl N-(2-chloro-4-bromobenzoyl)-L-glutamate, m.p. 77°–80° C.

The halobenzoic acid starting materials in turn can be prepared according to the following procedure:

To 8.1 g (51.3 mmol) of potassium permangante in 150 mL of water are added 5.0 g (21.1 mmol) of 2-fluoro-5-iodotoluene. The reaction mixture is heated at reflux for 4 hours. After being cooled to room temperature, the reaction mixture is poured into 250 mL of methylene chloride of sodium bisulfate, and 1N hydrochloric acid. The organic layer is separated, washed with water and dried over sodium sulfate. The solvent is removed in vacuo and the solid triturated with hexane to give 0.86 g (15%) of 2-fluoro-5-iodobenzoic acid as a white solid, m.p. 161°–163° C.

2-Fluoro-4-iodobenzoic acid, m.p. 213–215° C. (dec) is similarly prepared from 2-fluoro-4-iodotoluene.

What is claimed is:

1. A compound selected from the group consisting of (i) a tetrahydro[2,3-d]pyrimidine the formula:

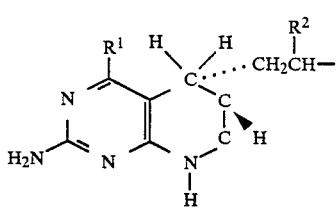

-continued

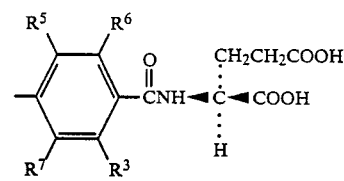

wherein R$^1$ is hydroxy or amino;

R$^2$ is hydrogen, methyl, or ethyl;

one or two members of R$^3$, R$^5$, R$^6$, and R$^7$ are selected from the group consisting of chloro and fluoro and the remaining members of R$^3$, R$^5$, R$^6$, and R$^7$ are hydrogen;

(ii) the pharmaceutically acceptable salts thereof; and (iii) diastereoisomeric mixtures of said tetrahydro[2,3-d]pyrimidines or their salts.

2. A compound according to claim 1 wherein R$^1$ is hydroxy and R$^2$ is hydrogen.

3. A compound according to claim 2 wherein one of R$^3$, R$^5$, R$^6$, and R$^7$ is chloro or fluoro and the remaining members of R$^3$, R$^5$, R$^6$, and R$^7$ are each hydrogen.

4. A compound according to claim 3 which is N-(2-chloro-4-[2-(2-amino-4-hydroxy-5,6,7,8-tetrahydropyrido[2,3-d]pyrimidin-6-yl)ethyl]benzoyl)-L-glutamic acid.

5. A compound according to claim 3 which is N-(2-fluoro-4-[2-(2-amino-4-hydroxy-5,6,7,8-tetrahydropyrido[2,3-d]pyrimidin-6-yl)ethyl]benzoyl)-L-glutamic acid.

6. The method of inhibiting neoplastic growth in a mammal which growth is dependent on folic acid or a metabolic derivative of folic acid as a substrate, which comprises administering to the mammal in a single or multiple dose regimen an effective amount of a compound according to claim 1.

7. A pharmaceutical composition for inhibiting neoplastic growth in a mammal which growth is dependent on folic acid or a metabolic derivative of folic acid as a substrate, which comprises an amount of a compound according to claim 1 which upon administration to the mammal in a single or multiple dose regiment is effective to inhibit said growth, in combination with a pharmaceutically acceptable carrier.

8. A compound selected from the group consisting of (i) a tetrahydro[2,3-d]pyrimidine the formula:

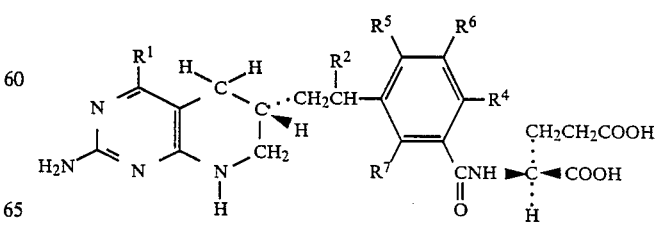

or

-continued

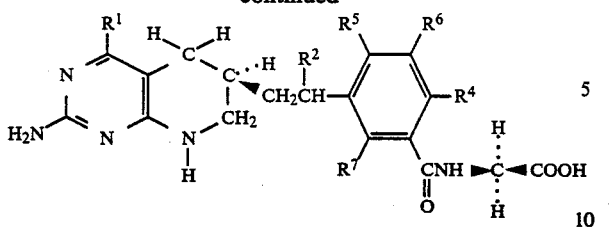

wherein $R^1$ is hydroxy or amino;
$R^2$ is hydrogen, methyl, or ethyl;
none, one or two members of $R^4$, $R^5$, $R^6$, and $R^7$ are selected from the group consisting of chloro and fluoro and the remaining members of $R^4$, $R^5$, $R^6$, and $R^7$ are hydrogen;
(ii) the pharmaceutically acceptable salts thereof; and
(iii) diastereoisomeric mixtures of said tetrahydro[2,3-d]pyrimidines or their salts.

9. A compound according to claim 8 wherein $R^1$ is hydroxy and $R^2$ is hydrogen.

10. A compound according to claim 9 wherein one of $R^4$, $R^5$, $R^6$, and $R^7$ is hydrogen, chloro, or fluoro, and the remaining members of $R^4$, $R^5$, $R^6$, and $R^7$ are each hydrogen.

11. A compound according to claim 10 which is N-(3-[2-(2-amino-4-hydroxy-5,6,7,8-tetrahydropyrido-[2,3-d]pyrimidin-6-yl)ethyl]benzoyl)-L-glutamic acid.

12. A compound according to claim 10 which is N-(2-fluoro-5-[2-(2-amino-4-hydroxy-5,6,7,8-tetrahydropyrido[2,3-d]pyrimidin-6-yl)ethyl]benzoyl)-L-glutamic acid.

13. The method of inhibiting neoplastic growth in a mammal which growth is dependent on folic acid or a metabolic derivative of folic acid as a substrate, which comprises administering to the mammal in a single or multiple dose regimen an effective amount of a compound according to claim 8.

14. A pharmaceutical composition for inhibiting neoplastic growth in a mammal which growth is dependent on folic acid or a metabolic derivative of folic acid as a substrate, which comprises an amount of a compound according to claim 8 which upon administration to the mammal in a single or multiple dose regimen is effective to inhibit said growth, in combination with a pharmaceutically acceptable carrier.

* * * * *

UNITED STATES PATENT AND TRADEMARK OFFICE
CERTIFICATE OF CORRECTION

PATENT NO. : 4,889,859

DATED : December 26, 1989

INVENTOR(S) : Edward C. Taylor et al.

It is certified that error appears in the above-identified patent and that said Letters Patent is hereby corrected as shown below:

Claim 1 should read as follows:

1. A compound selected from the group consisting of (i) a tetrahydro[2,3-d]pyrimidine the formula:

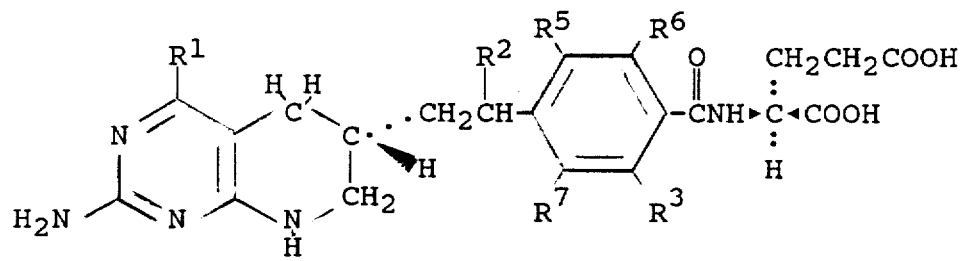

or

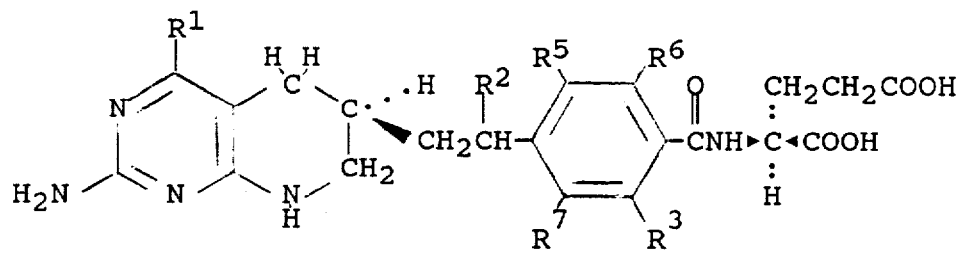

wherein $R^1$ is hydroxy or amino;

$R^2$ is hydrogen, methyl, or ethyl;

UNITED STATES PATENT AND TRADEMARK OFFICE
CERTIFICATE OF CORRECTION

PATENT NO. : 4,889,859

DATED : December 26, 1989

INVENTOR(S) : Edward C. Taylor et al.

It is certified that error appears in the above-identified patent and that said Letters Patent is hereby corrected as shown below:

- 2 -

Claim 1 . . . (cont'd)

one or two members of $R^3$, $R^5$, $R^6$, and $R^7$ are selected from the group consisting of chloro and fluoro and the remaining members of $R^3$, $R^5$, $R^6$, and $R^7$ are hydrogen;

(ii) the pharmaceutically acceptable salts thereof; and (iii) diastereoisomeric mixtures of said tetrahydro[2,3-d]pyrimidines or their salts.

Signed and Sealed this

Twenty-second Day of January, 1991

Attest:

HARRY F. MANBECK, JR.

Attesting Officer     Commissioner of Patents and Trademarks

UNITED STATES PATENT AND TRADEMARK OFFICE
CERTIFICATE OF CORRECTION

PATENT NO. : 4,889,859

DATED : DECEMBER 26, 1989

INVENTOR(S) : EDWARD C. TAYLOR and CHUAN SHIH

It is certified that error appears in the above-indentified patent and that said Letters Patent is hereby corrected as shown below:

Cols. 12, lines 54-66 and Col. 13, lines 1-10,

Claim 8 chould read as follows:

8. A compound selected from the group consisting of
(i) a tetrahydro[2,3-d]pyrimidine the formula:

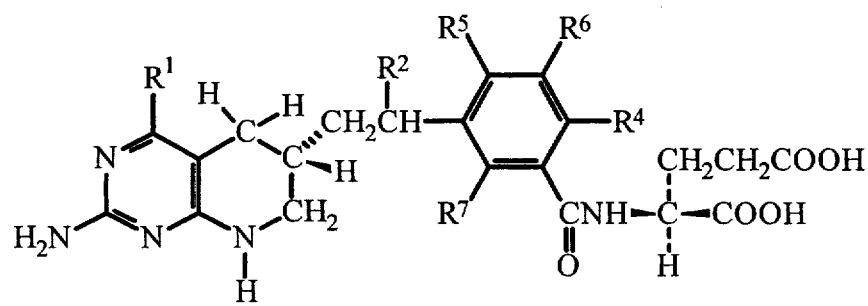

or

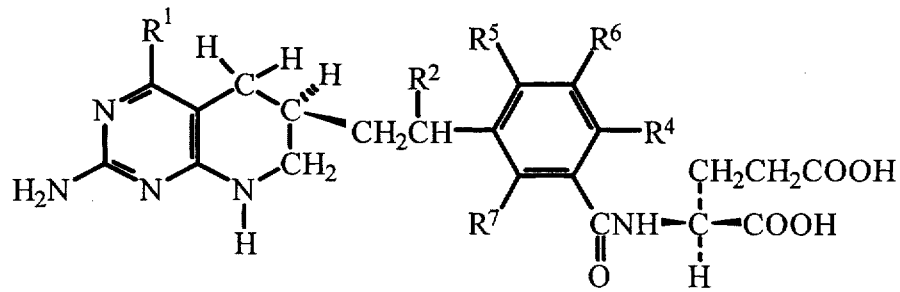

UNITED STATES PATENT AND TRADEMARK OFFICE
CERTIFICATE OF CORRECTION

PATENT NO.   : 4,889,859
DATED        : DECEMBER 26, 1989
INVENTOR(S)  : EDWARD C. TAYLOR and CHUAN SHIH It is certified that error appears in the above-indentified patent and that said Letters Patent is hereby corrected as shown below:

> wherein $R^1$ is hydroxy or amino;
>
> $R^2$ is hydrogen, methyl, or ethyl;
>
> none, one or two members of $R^4$, $R^5$, $R^6$, and $R^7$ are selected from the group consisting of chloro and fluoro and the remaining members of $R^4$, $R^5$, $R^6$, and $R^7$ are hydrogen;

(ii) the pharmaceutically acceptable salts thereof, and (iii) diastereoisomeric mixtures of said tetrahydro[2,3-d]pyrimidines or their salts.

Signed and Sealed this

Twenty-first Day of October 1997

Attest:

BRUCE LEHMAN

Attesting Officer

Commissioner of Patents and Trademarks